(12) United States Patent
Hegemann (10) Patent No.: US 6,472,184 B1
(45) Date of Patent: Oct. 29, 2002

(54) METHOD FOR PRODUCING NUCLEIC ACID POLYMERS

(76) Inventor: Peter Hegemann, Hauptstrasse 40, Friesheim (DE), D-98092

(*) Notice: Subject to any disclaimer, the term of this patent is extended or adjusted under 35 U.S.C. 154(b) by 0 days.

(21) Appl. No.: 09/486,241
(22) PCT Filed: Aug. 17, 1998
(86) PCT No.: PCT/EP98/05219
§ 371 (c)(1),
(2), (4) Date: May 12, 2000
(87) PCT Pub. No.: WO99/10358
PCT Pub. Date: Mar. 4, 1999

(30) Foreign Application Priority Data

Aug. 22, 1997 (DE) .......................................... 197 36 591

(51) Int. Cl.$^7$ .......................... C12P 19/34; C07H 21/04; C12Q 1/68; A61K 38/00; C07K 16/00
(52) U.S. Cl. .......................... 435/91.1; 435/6; 435/91.1; 435/91.2; 536/23.1; 536/243; 536/24.33; 536/25.3; 530/334
(58) Field of Search .......................... 435/6, 91.1, 91.2; 536/25.3, 23.1, 24.3, 24.33; 530/334

(56) References Cited

U.S. PATENT DOCUMENTS

| | | | | |
|---|---|---|---|---|
| 5,679,773 A | * | 10/1997 | Holmes ...................... | 530/334 |
| 5,969,128 A | * | 10/1999 | De Vos et al. ............. | 536/25.3 |
| 6,110,668 A | * | 8/2000 | Strizhov et al. ............. | 435/6 |
| 6,239,265 B1 | * | 5/2001 | Cook ........................ | 536/23.1 |

FOREIGN PATENT DOCUMENTS

WO  WO 98/15567  4/1998

OTHER PUBLICATIONS

Chen et al., 3–Biochem Genetics, Abstract 114:37139a, 114:209, 1991.
Dunn et al., Analytical Biochemistry, 228:91–100, 1995.
Strizhov et al., Proc. Natl. Acad. Sci. USA, 93:15012–15017, 1996.

* cited by examiner

Primary Examiner—Jeffrey Fredman
Assistant Examiner—Arun Chakrabarti
(74) Attorney, Agent, or Firm—Darby & Darby (57) ABSTRACT

The conventional synthesis of nucleic acid polymers from several oligonucleotides comprises several cycles of intermediate product synthesis, purification of the intermediate products and synthesis of a full length product (up to a maximum length of approximately 1000 nucleotides). The novel method shall be carried out in one reaction step and result in nucleic acid polymers of more than 1000 nucleotides.

According to the invention, two or more linkable oligonucleotides are provided that in a continuous arrangement and after linkage can form a primary strand, and one or more non-linkable oligonucleotides are provided, each of the non-linkable oligonucleotides comprising two adjoining regions, the first of which is complementary to the 3' end of a linkable oligonucleotide and the second of which is complementary to the 5' end of a further linkable oligonucleotide. The linkable oligonucleotides are hybridized with the complementary regions of the non-linkable oligonucleotides and then linked enzymatically, chemically or photochemically.

The method is suited for the de novo synthesis of long nucleic acid chains.

32 Claims, 5 Drawing Sheets

FG1 (46)   ATGGCCAAGGGCGAGGAGCTGTTCACCGGTGTGGTCCCCATCCTGG
FG2 (46)   TGGAGCTGGACGGGCGACGTGAACGCCACAAGTTCTCCGTCTCCGG
FG3 (46)   CGAGGGTGAGGGTGACGCCACCTACGGCAAGCTGACCCTGAAGTTC
FG4 (45)   ATCTGCACCACCGGCAAGCTGCCCGTGCCCTGGCCCACCCTGGTC
FG5 (46)   ACCACCCTGACCTACGGTGTGCAGTGCTTCTCCCGCTACCCCGACC
FG6 (47)   ACATGAAGCAGCACGACTTCTTCAAGTCCGCCATGCCCGAGGGCTAC
FG7 (47)   GTGCAGGAGGCCACCATCTTCTTCAAGGACGACGGCAACTACAAGAC
FG8 (45)   CCGCGCCGAGGTCAAGTTCGAGGGCGACACCCTGGTGAACCGCAT
FG9 (45)   CGAGCTGAAGGGCATCGACTTCAAGGAGGACGGCAACATCCTGGG
FG10 (47)  CCACAAGCTGGAGTACAACTACAACTCCCACAACGTGTACATCATGG
FG11 (47)  CCGACAAGCAGAAGAACGGCATCAAGGTGAACTTCAAGATCCGCCAC
FG12 (45)  AACATCGAGGACGGCTCCGTGCAGCTGGCCGACCACTACCAGCAG
FG13 (46)  AACACCCCCATCGGCGATGGCCCCGTGCTGCTGCCCGACAACCACT
FG14 (46)  ACCTGTCCACCCAGTCCGCCCTGTCCAAGGACCCCAACGAGAAGCG
FG15 (46)  CGACCACATGGTCCTGCTGGAGTTCGTCACCGCTGCCGGCATCACC

FIG. 5a

FG14rev(46)  ACTCCAGCAGGACCATGTGGTCGCGCTTCTCGTTGGGTCCTTGGA
FG13rev(46)  CAGGGGCGGACTGGGTGGACAGGTAGTGGTTGTCGGGCAGCAGCACG
FG12rev(46)  GGGCCATGCCGATGGGGGTGTTCTGCTGGTAGTGGTCGGCCAGCT
FG11rev(46)  GCACGGAGCCGTCCTCGATGTTGTGGGCGGATCTTGAAGTTCACCTT
FG10rev(46)  GATGCCGTTCTTCTGCTTGTGCGGCCATGATGTACACGTGTGGGAG
FG9rev(46)   TTGTAGTTGTACTCCAGCTTGTGGCCCAGGATGTTGCCGTCCTCCT
FG8rev(46)   TGAAGTCGATGCCCTTCAGCTCGATGCGGTTCACCAGGGTGTCGCC
FG7rev(46)   CTCGAACTTGACCTCGGCGCGGGTCTTGTAGTTGCCGTCGTCCTTG
FG6rev(46)   AAGAAGATGGTGCGCTCCTGCACGTAGCCCTCGGGCATGGCGGACT
FG5rev(46)   TGAAGAAGTCGTCGTGCTTCATGTGGTCGGGGTAGCGGGAGAAGCA
FG4rev(46)   CTGCACACCGTAGGTCAGGGTGGTGACCAGGGTGGGCCAGGGCACG
FG3rev(46)   GGCAGCTTGCCGGTGTGCAGATGAACTTCAGGGTCAGCTTGCCGT
FG2rev(46)   AGGTGGCGTCACCCTCACCCTCGCCGGAGACGGAGAACTTGTGGCC
FG1rev(46)   GTTCACGTCGCCGTCCAGCTCCACCAGGATGGGGACCACACCGGTG

FIG. 5b

FG15rev(50)  TTACTTGTACAGCTCGTCCATGCCGTGGGTGATGCCGGCAGCGGTGACGA

FIG. 5c

ATGTCCAAGGGCGAGGAGCTGTTCACCGGGGTGTGGTCCCCATCCTGGTGGAGCTGGA
CGGCGACGTGAACGGCCACAAGTTCTCCGTCTCCGGCGAGGGTGAGGGTGACGCCA
CCTACGGCAAGCTGACCCTGAAGTTCATCTGCACCACCGGCAAGTCGCCCGTGCCC
TGGCCCACCCTGGTCACCACCTTCACCTACGGTGTGCAGTGCTTCTCCCGCTACCC
CGACCATATGAAGCAGCACGACTTCTTCAAGTCCGCCATGCCCGAGGGCTACGTGC
AGGAGCGCACCATCTTCTTCAAGGACGACGGCAACTACAAGACCCGCGCCGAGGTC
AAGTTCGAGGGCGACACCCTGGTGAACCGCATCGAGCTGAAGGGCATCGACTTCAA
GGAGGACGGCAACATCCTGGGGCACAAGCTGGAGTACAACTACAACTCCCACAACG
TGTACATCATGGCCGACAAGCAGAAGAACGGCATCAAGGTGAACTTCAAGATCCGC
CACAACATCGAGGACGGCAGCGTCCAGCTGGCCGACCACTACCAGCAGAACACCCC
CATCGGCGATGGCCCTGTGCTGCTGCCCGACAACCACTACCTGTCCACCCAGTCCG
CCCTGTCCAAGGACCCCAACGAGAAGCGCGACCATGGTCCTGCTGGAGTTCGTC
ACCGCTGCCGGGCATCACCACCGGCATGGATGAGCTGTACAAGTAA

Fig. 6

SEQUENCE LISTING

<160> NUMBER OF SEQ ID NOS: 33

<210> SEQ ID NO 1
<211> LENGTH: 46
<212> TYPE: DNA
<213> ORGANISM: Artificial Sequence
<220> FEATURE:
<223> OTHER INFORMATION: Primer -continued

```
<400> SEQUENCE: 1
atggccaagg gcgaggagct gttcaccggt gtggtcccca tcctgg         46

<210> SEQ ID NO 2
<211> LENGTH: 46
<212> TYPE: DNA
<213> ORGANISM: Artificial Sequence
<220> FEATURE:
<223> OTHER INFORMATION: Primer

<400> SEQUENCE: 2
tggagctgga cggcgacgtg aacggccaca agttctccgt ctccgg         46

<210> SEQ ID NO 3
<211> LENGTH: 46
<212> TYPE: DNA
<213> ORGANISM: Artificial Sequence
<220> FEATURE:
<223> OTHER INFORMATION: Primer

<400> SEQUENCE: 3
cgagggtgag ggtgacgcca cctacggcaa gctgaccctg aagttc         46

<210> SEQ ID NO 4
<211> LENGTH: 45
<212> TYPE: DNA
<213> ORGANISM: Artificial Sequence
<220> FEATURE:
<223> OTHER INFORMATION: Primer

<400> SEQUENCE: 4
atctgcacca ccggcaagct gcccgtgccc tggcccaccc tggtc          45

<210> SEQ ID NO 5
<211> LENGTH: 46
<212> TYPE: DNA
<213> ORGANISM: Artificial Sequence
<220> FEATURE:
<223> OTHER INFORMATION: Primer

<400> SEQUENCE: 5
accaccctga cctacggtgt gcagtgcttc tcccgctacc ccgacc         46

<210> SEQ ID NO 6
<211> LENGTH: 47
<212> TYPE: DNA
<213> ORGANISM: Artificial Sequence
<220> FEATURE:
<223> OTHER INFORMATION: Primer

<400> SEQUENCE: 6
acatgaagca gcacgacttc ttcaagtccg ccatgcccga gggctac        47

<210> SEQ ID NO 7
<211> LENGTH: 47
<212> TYPE: DNA
<213> ORGANISM: Artificial Sequence
<220> FEATURE:
<223> OTHER INFORMATION: Primer

<400> SEQUENCE: 7
gtgcaggagc gcaccatctt cttcaaggac gacggcaact acaagac        47

<210> SEQ ID NO 8
<211> LENGTH: 45
```

-continued

<212> TYPE: DNA
<213> ORGANISM: Artificial Sequence
<220> FEATURE:
<223> OTHER INFORMATION: Primer

<400> SEQUENCE: 8
ccgcgccgag gtcaagttcg agggcgacac cctggtgaac cgcat         45

<210> SEQ ID NO 9
<211> LENGTH: 45
<212> TYPE: DNA
<213> ORGANISM: Artificial Sequence
<220> FEATURE:
<223> OTHER INFORMATION: Primer

<400> SEQUENCE: 9
cgagctgaag ggcatcgact tcaaggagga cggcaacatc ctggg         45

<210> SEQ ID NO 10
<211> LENGTH: 47
<212> TYPE: DNA
<213> ORGANISM: Artificial Sequence
<220> FEATURE:
<223> OTHER INFORMATION: Primer

<400> SEQUENCE: 10
ccacaagctg gagtacaact acaactccca caacgtgtac atcatgg       47

<210> SEQ ID NO 11
<211> LENGTH: 47
<212> TYPE: DNA
<213> ORGANISM: Artificial Sequence
<220> FEATURE:
<223> OTHER INFORMATION: Primer

<400> SEQUENCE: 11
ccgacaagca gaagaacggc atcaaggtga acttcaagat ccgccac       47

<210> SEQ ID NO 12
<211> LENGTH: 45
<212> TYPE: DNA
<213> ORGANISM: Artificial Sequence
<220> FEATURE:
<223> OTHER INFORMATION: Primer

<400> SEQUENCE: 12
aacatcgagg acggctccgt gcagctggcc gaccactacc agcag         45

<210> SEQ ID NO 13
<211> LENGTH: 46
<212> TYPE: DNA
<213> ORGANISM: Artificial Sequence
<220> FEATURE:
<223> OTHER INFORMATION: Primer

<400> SEQUENCE: 13
aacaccccca tcggcgatgg ccccgtgctg ctgcccgaca accact        46

<210> SEQ ID NO 14
<211> LENGTH: 46
<212> TYPE: DNA
<213> ORGANISM: Artificial Sequence
<220> FEATURE:
<223> OTHER INFORMATION: Primer

<400> SEQUENCE: 14
acctgtccac ccagtccgcc ctgtccaagg accccaacga gaagcg         46

<210> SEQ ID NO 15
<211> LENGTH: 46
<212> TYPE: DNA
<213> ORGANISM: Artificial Sequence
<220> FEATURE:
<223> OTHER INFORMATION: Primer

<400> SEQUENCE: 15
cgaccacatg gtcctgctgg agttcgtcac cgctgccggc atcacc         46

<210> SEQ ID NO 16
<211> LENGTH: 46
<212> TYPE: DNA
<213> ORGANISM: Artificial Sequence
<220> FEATURE:
<223> OTHER INFORMATION: Primer

<400> SEQUENCE: 16
actccagcag gaccatgtgg tcgcgcttct cgttggggtc cttgga         46

<210> SEQ ID NO 17
<211> LENGTH: 46
<212> TYPE: DNA
<213> ORGANISM: Artificial Sequence
<220> FEATURE:
<223> OTHER INFORMATION: Primer

<400> SEQUENCE: 17
cagggcggac tgggtggaca ggtagtggtt gtcgggcagc agcacg         46

<210> SEQ ID NO 18
<211> LENGTH: 46
<212> TYPE: DNA
<213> ORGANISM: Artificial Sequence
<220> FEATURE:
<223> OTHER INFORMATION: Primer

<400> SEQUENCE: 18
gggccatcgc cgatgggggt gttctgctgg tagtggtcgg ccagct         46

<210> SEQ ID NO 19
<211> LENGTH: 46
<212> TYPE: DNA
<213> ORGANISM: Artificial Sequence
<220> FEATURE:
<223> OTHER INFORMATION: Primer

<400> SEQUENCE: 19
gcacggagcc gtcctcgatg ttgtggcgga tcttgaagtt cacctt         46

<210> SEQ ID NO 20
<211> LENGTH: 46
<212> TYPE: DNA
<213> ORGANISM: Artificial Sequence
<220> FEATURE:
<223> OTHER INFORMATION: Primer

<400> SEQUENCE: 20
gatgccgttc ttctgcttgt cggccatgat gtacacgttg tgggag         46

<210> SEQ ID NO 21
<211> LENGTH: 46

```
<212> TYPE: DNA
<213> ORGANISM: Artificial Sequence
<220> FEATURE:
<223> OTHER INFORMATION: Primer

<400> SEQUENCE: 21
ttgtagttgt actccagctt gtggcccagg atgttgccgt cctcct          46

<210> SEQ ID NO 22
<211> LENGTH: 46
<212> TYPE: DNA
<213> ORGANISM: Artificial Sequence
<220> FEATURE:
<223> OTHER INFORMATION: Primer

<400> SEQUENCE: 22
tgaagtcgat gcccttcagc tcgatgcggt tcaccagggt gtcgcc          46

<210> SEQ ID NO 23
<211> LENGTH: 46
<212> TYPE: DNA
<213> ORGANISM: Artificial Sequence
<220> FEATURE:
<223> OTHER INFORMATION: Primer

<400> SEQUENCE: 23
ctcgaacttg acctcggcgc gggtcttgta gttgccgtcg tccttg          46

<210> SEQ ID NO 24
<211> LENGTH: 46
<212> TYPE: DNA
<213> ORGANISM: Artificial Sequence
<220> FEATURE:
<223> OTHER INFORMATION: Primer

<400> SEQUENCE: 24
aagaagatgg tgcgctcctg cacgtagccc tcgggcatgg cggact          46

<210> SEQ ID NO 25
<211> LENGTH: 46
<212> TYPE: DNA
<213> ORGANISM: Artificial Sequence
<220> FEATURE:
<223> OTHER INFORMATION: Primer

<400> SEQUENCE: 25
tgaagaagtc gtgctgcttc atgtggtcgg ggtagcggga gaagca          46

<210> SEQ ID NO 26
<211> LENGTH: 46
<212> TYPE: DNA
<213> ORGANISM: Artificial Sequence
<220> FEATURE:
<223> OTHER INFORMATION: Primer

<400> SEQUENCE: 26
ctgcacaccg taggtcaggg tggtgaccag ggtgggccag ggcacg          46

<210> SEQ ID NO 27
<211> LENGTH: 46
<212> TYPE: DNA
<213> ORGANISM: Artificial Sequence
<220> FEATURE:
<223> OTHER INFORMATION: Primer
```

<400> SEQUENCE: 27
ggcagcttgc cggtggtgca gatgaacttc agggtcagct tgccgt         46

<210> SEQ ID NO 28
<211> LENGTH: 46
<212> TYPE: DNA
<213> ORGANISM: Artificial Sequence
<220> FEATURE:
<223> OTHER INFORMATION: Primer

<400> SEQUENCE: 28
aggtggcgtc accctcaccc tcgccggaga cggagaactt gtggcc         46

<210> SEQ ID NO 29
<211> LENGTH: 46
<212> TYPE: DNA
<213> ORGANISM: Artificial Sequence
<220> FEATURE:
<223> OTHER INFORMATION: Primer

<400> SEQUENCE: 29
gttcacgtcg ccgtccagct ccaccaggat ggggaccaca ccggtg         46

<210> SEQ ID NO 30
<211> LENGTH: 50
<212> TYPE: DNA
<213> ORGANISM: Artificial Sequence
<220> FEATURE:
<223> OTHER INFORMATION: Primer

<400> SEQUENCE: 30
ttacttgtac agctcgtcca tgccgtgggt gatgccggca gcggtgacga     50

<210> SEQ ID NO 31
<211> LENGTH: 717
<212> TYPE: DNA
<213> ORGANISM: Artificial Sequence
<220> FEATURE:
<223> OTHER INFORMATION: Modified gene from Aquorea victorea

<400> SEQUENCE: 31
atgtccaagg gcgaggagct gttcaccggt gtggtcccca tcctggtgga gctggacggc     60
gacgtgaacg gccacaagtt ctccgtctcc ggcgagggtg agggtgacgc cacctacggc    120
aagctgaccc tgaagttcat ctgcaccacc ggcaagctgc ccgtgccctg cccacccctg    180
gtcaccacct tcacctacgg tgtgcagtgc ttctcccgct accccgacca catgaagcag    240
cacgacttct tcaagtccgc catgcccgag ggctacgtgc aggagcgcac catcttcttc    300
aaggacgacg gcaactacaa gacccgcgcc gaggtcaagt tcgagggcga caccctggtg    360
aaccgcatcg agctgaaggg catcgacttc aaggaggacg gcaacatcct gggccacaag    420
ctggagtaca actacaactc ccacaacgtg tacatcatgg ccgacaagca gaagaacggc    480
atcaaggtga acttcaagat ccgccacaac atcgaggacg gctccgtgca gctggccgac    540
cactaccagc agaacacccc catcggcgat ggccccgtgc tgctgcccga caaccactac    600
ctgtccaccc agtccgccct gtccaaggac cccaacgaga gcgcgacca catggtcctg    660 ctggagttcg tcaccgctgc cggcatcacc cacggcatgg acgagctgta caagtaa     717

<210> SEQ ID NO 32
<211> LENGTH: 30
<212> TYPE: DNA
<213> ORGANISM: Artificial Sequence -continued

```
<220> FEATURE:
<223> OTHER INFORMATION: Primer

<400> SEQUENCE: 32
ccgctcgaga tggccaaggg cgaggagctg                                      30

<210> SEQ ID NO 33
<211> LENGTH: 33
<212> TYPE: DNA
<213> ORGANISM: Artificial Sequence
<220> FEATURE:
<223> OTHER INFORMATION: Primer

<400> SEQUENCE: 33
cgcggatcct tacttgtaca gctcgtccat gcc                                  33
```

METHOD FOR PRODUCING NUCLEIC ACID POLYMERS

FIELD OF THE INVENTION

The present invention relates to a method for producing nucleic acid polymers.

BACKGROUND OF THE INVENTION

The increasing use of recombinant genes in genetic engineering and biotechnology and in the medical analytical field has created a great demand for methods of the "de novo" synthesis of long nucleic acid chains. In many cases the synthetic production of arbitrarily chosen nucleic acid sequences can be a time-saving alternative to troublesome cloning and modifying methods. A routine synthesis of long nucleic acid chains can also offer decisive advantages in the case of "drug design", e.g. in the production of "custom-made" antibodies, inhibitor/activator molecules, ribozymes, or in DNA chip technology. Furthermore, purposefully modified nucleotides, e.g. labeled by (fluorescent) dyes or enzymes, could be incorporated into a nucleic acid chain in this way. Apart from the examples given here, there are many further possible applications for purposefully produced nucleic acid polymers.

In the simplest variant of conventional gene synthesis, i.e. direct cloning, two long oligonucleotides which are fully complementary to each other are hybridized with one another. On account of the present technical limitation in the production of oligonucleotides to a length of 150 to 200 bases, the size of the resultant hybridization products is also limited to such a range of length.

A further method for producing long nucleic acid polymers is the so-called fill-in method in which two single-stranded nucleic acid chains are hybridized with each other, and protruding ends are filled with the help of DNA polymerases so that the double-stranded product is longer than the oligonucleotides used. However, even with the fill-in method, it is not possible to produce a product that is longer than the sum of the nucleic acid chains used.

In the "shot-gun gene synthesis" complementary single-stranded oligonucleotides are directly transfected into cells together with an expression vector which has been opened by restriction enzymes, and a circularized product can here only be obtained if all of the partial sequences are ligated by the enzyme machinery of the host organism in a suitable way. The efficiency of successful ligations in this method is in general very limited, in particular when many oligonucleotides are used for gene synthesis.

In 1972 Khorana developed a method named after him, in which several chemically synthetized oligonucleotides of an average length of 15 nucleotides, which in a suitable arrangement are overlapping without any gaps, were enzymatically joined by polynucleotide ligase to obtain a double strand (Khorana, H. G. et al., J. Mol. Biol. 27, 209–17, 1972, and follow-up publications; Khorana, H. G. et al., J. Biol. Chem. 251, 3(10), 565–70, 1976 and follow-up publications). Sequential ligation of a few (4–8) oligonucleotides for obtaining longer intermediate products, purification of the intermediate products and subsequent ligation of the intermediate products with one another resulted in the synthesis of double-stranded nucleic acid chains with a length of 514 base pairs (Edge, M. D. et al., Nature 292, 756–62, 1981), later with a length of up to about 1000 bp, which could subsequently be cloned in bacterial expression vectors.

These methods have several decisive drawbacks:

1.) After each ligation step the products or intermediate products had to be purified by separation on a polyacrylamide gel (PAA gel) to eliminate undesired by-products of the ligation reaction. Such a time-intensive working step requires great efforts with respect to personnel and costs.

2.) During elution of the intermediate and final products from the PAA gel considerable losses in yield had to be accepted.

3.) The so far longest product that could be produced with the help of said technique had a length of about 1000 base pairs. Since most of the eukaryotic and prokaryotic genes have a coding sequence of 300 to 3000 base pairs on the average, such a length is not sufficient for most applications.

4.) For the necessary purification via PAA gels the nucleotides were normally radioactively labeled in the method described by Khorana to be able to identify the bands of the desired products in the gel. The use of highly radioactive $^{32}P$ labels constitutes a potential risk which could not be avoided in said method.

OBJECT OF THE INVENTION

It is therefore the object of the present invention to provide an uncomplicated, reliable and inexpensive method for the synthesis of nucleic acid polymers of a length of more than 1000 bases in one step, wherein the above-mentioned drawbacks can be overcome.

DETAILED DESCRIPTION OF THE INVENTION

Said object is achieved by a method for producing a nucleic acid polymer, comprising the following steps:

a) providing 2 or more linkable oligonucleotides which in a continuous arrangement and after linkage can form a primary strand, and one or more non-linkable oligonucleotides, each of the non-linkable oligonucleotides comprising two adjoining regions the first of which is complementary to the 3' end of a linkable oligonucleotide and the second of which is complementary to the 5' end of a further linkable oligonucleotide, b) hybridizing oligonucleotides for the primary strand with the complementary regions of the non-linkable oligonucleotides, and c) linking the oligonucleotides of the primary strand.

Figure 1:
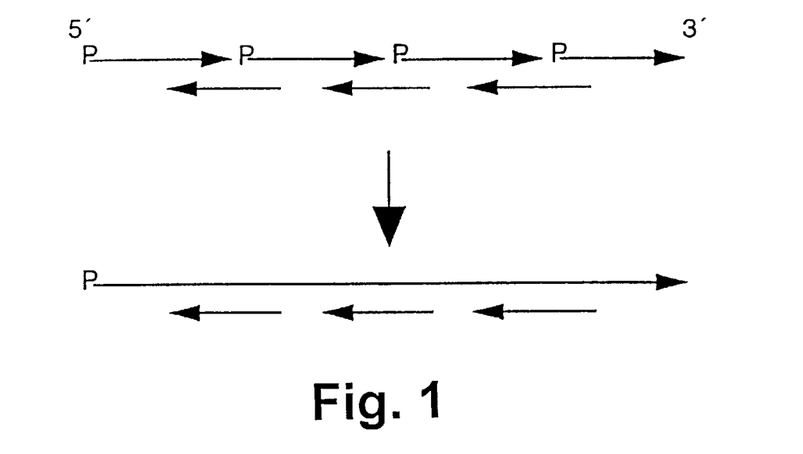
FIG. 1 depicts a preferred embodiment of the method according to the invention.
Figure 2:
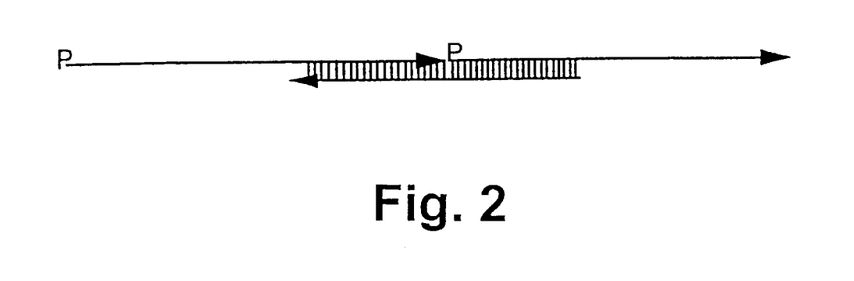
FIG. 2 is a detail view showing the overlapping region between two adjacent linkable oligonucleotides and one non-linkable oligonucleotide that comprises two adjoining regions of which one is complementary to the 3' end of a first linkable oligonucleotide, and of which the second one is complementary to the 5' end of a second linkable oligonucleotide. The overlapping region between a region of the non-linkable oligonucleotide and the complementary region of one of the linkable oligonucleotoides should be at least 15 bp.

The method according to the invention is schematically shown in FIGS. 1 and 2. In contrast to the Khorana method, it offers the decisive advantage that the synthesis of a single-stranded nucleic acid polymer can be carried out in a single reaction batch. All of the linkable and non-linkable oligonucleotides that are required for the synthesis of the primary strand are here used at the same time; the addition of a linker yields a primary strand of covalently linked oligonucleotides which can reach a length of more than 1000, e.g. 1500, bases.

In preferred embodiments steps (b) and (c) are repeated several times, and the oligonucleotides which were previously hybridized with one another are separated from each other prior to each repetition of said two steps, i.e. the double strand previously formed by hybridization is denatured. Denaturation can be carried out by increasing the temperature or by increasing the pH in the manner known to one skilled in the art. The repeated denaturation and renaturation with subsequent linking considerably improves the yield in primary strand which, otherwise, is e.g. impaired by chain terminations which are the result of the incorporation of incompletely phosphorylated primary strand oligonucleotides. The influence of such chain terminations on the total yield is minimized by repeating steps (b) and (c).

According to the invention steps (b) and (c) are carried out not only once, but several times. In a preferred embodiment, they are repeated 1 to 8 times, particularly preferably 3 to 5 times.

The number of the oligonucleotides used can vary between 2 linkable oligonucleotides and 150 linkable oligonucleotides. The number of the non-linkable oligonucleotides is always equal to the number of the linkable oligonucleotides, by one higher or by one lower, i.e. at least one. Between 5 and 100 linkable oligonucleotides are preferably used; particularly preferably between 10 and 50 linkable oligonucleotides.

The linking of the linkable oligonucleotides of the primary strand may comprise various reactions. In this instance linking means e.g. a reaction of an enzymatic, chemical or also photochemical kind. For instance in the case of enzymatic linking (ligation), T4 DNA ligase is e.g. used as the linker. In the preferred embodiment, use is made of a thermostable ligase, e.g. Pfu ligase (Stratagene) which offers the advantage that in the case of repeated cycles of denaturation by way of temperature increase, hybridization and ligation of the oligonucleotides, no new enzyme has to be added whereas this is the case when thermolabile DNA ligases, such as T4 DNA ligase, are used.

Furthermore, the use of said thermostable ligase makes it possible to carry out the steps of hybridizing and ligating the oligonucleotides at high temperatures of 45° C. to 80° C., preferably 70° C. Such stringent temperature conditions mean that the step of hybridizing the oligonucleotides is carried out in a complementary arrangement with a high specifity and that the amount of by-products obtained is considerably smaller than in the Khorana method. Ligations with conventional ligase are normally carried out within a temperature range of 40° C. to 4° C. and can thus lead to a higher amount of unspecific hybridizations by mispairing or secondary structures.

A chemical linkage of oligonucleotides, which has been described by Goeddel and colleagues (Goeddel, D. V. et al., PNAS 76, 1979), is also possible.

A further possibility of linking oligonucleotides with one another is photochemical linkage. In this process the oligonucleotides to be linked must be labeled at the terminal nucleotides with photosensitive molecules which contain carbon-carbon double bonds and may be subject to a (2+2) photocyclodimerization, e.g. stilbene, allene, mono-, di- and triene dicarboxylic acid derivatives or styrene derivatives.

According to the invention the non-linkable oligonucleotides just serve as a template for forming the nucleic acid polymer. In a preferred embodiment said oligonucleotides are not phosphorylated at their 5' end. As a result, an enzymatic linkage of said oligonucleotides, which are only responsible for the annealing of the linkable oligonucleotides in the desired arrangement, is not possible.

Non-linkable oligonucleotides can also be used in which e.g. the 3' end is a di-deoxynucleotide or a thionucleotide. Corresponding modifications are also possible at the 5' end. Furthermore, the method can be carried out with non-linkable oligonucleotides which are phosphorylated at the 3' end. Such a modification also prevents the enzymatic linkage of the oligonucleotides. Whenever the method of the invention is not carried out by means of enzymatic ligation, but is performed by way of chemical or photochemical linkage, the non-linkable oligonucleotides must be conceived accordingly in such a manner that under the conditions chosen for linking the olignucleotides forming the primary strand, they cannot form a covalent bond with the respectively adjacent non-linkable oligonucleotide.

The oligonucleotides used in the method of the invention may have a length of 30 to 1500 nucleotides. The length of the respectively selected nucleotide depends on several factors, including the probability of forming secondary structures and the purity of the selected start materials. However, it is preferred that the oligonucleotides of the primary strand have a length of 30 to 200, particularly preferably, 30 to 100 or 30 to 60 nucleotides.

Figure 3:
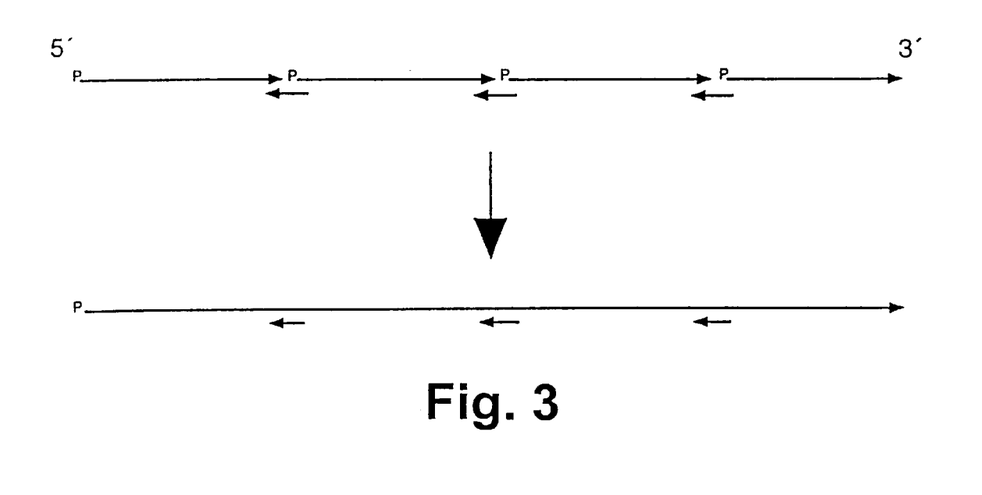
FIG. 3 illustrates the performance of the method with very long linkable oligonucleotides that are each correctly arranged side by side by way of hybridization with much shorter non-linkable oligonucleotides. For this purpose it suffices that the non-linkable oligonucleotides guarantee a stable hybridization with the two linkable oligonucleotides that must be arranged side by side, without the need for complementarity to the total and subsequent primary strand.

Single-stranded nucleic acid polymers already produced during synthesis can be combined in a further step, again with the method of the invention, to obtain single-stranded nucleic acid polymers having a length of several kilobases (FIG. 3). To this end, the method is carried out as described above, wherein nucleic acid polymers of e.g. 1500 bases can be used as linkable olignucleotides for the primary strand.

The non-linkable oligonucleotides which are to ensure a correct arrangement of the oligonucleotides of the primary strand side by side may optionally have a length of only 30 to 50 nucleotides. This order of magnitude permits hybridization with two oligonucleotides of the primary strand that are to be arranged side by side. Non-linkable oligonucleotides that cover the whole primary strand need not be provided for. However, the use of non-linkable oligonucleotides with up to 300 nucleotides or more is of course also possible and can certainly make sense in cases where strong secondary structures would otherwise be formed, for instance, in the primary strand.

Each of the non-linkable oligonucleotides contains two adjoining regions which exhibit complementarity to the 3' end and 5' end, respectively, of two adjacent oligonucleotides for the primary strand. The regions of complementarity between the linkable oligonucleotides for the primary strand and the non-linkable oligonucleotides of the complementary strand have each a length of about 15 to 30 base pairs, preferably 20 to 25 bp (see FIG. 2).

A preferred embodiment of the method consists in that in a preceding reaction the terminal oligonucleotides for the primary strand and/or oligonucleotides which are fully or partly complementary to the terminal oligonucleotides of the primary strand are annealed to the ends of a linearized vector, that they are linked with the vector and that subsequently the method set forth in claim 1 is carried out. The vector ends are here preferably cohesive. This method yields a circularized product which can directly be transfected into a suitable host organism, e.g. bacteria, mammal or insect cells. "Transfection" in this instance means various techniques, such a electroporation, microinjection, infection, transfection supported, for instance, by "Ca—$PO_4$", DEAE, hydrophobic molecules, etc.

In a preferred embodiment, either the 5' terminal oligonucleotide of the primary strand at its 5' end or the 3' terminal oligonucleotide of the primary strand at its 3' end is provided with a hapten, or both terminal oligonucleotides are provided with different haptens. This permits a fixation of the hapten-coupled oligonucleotide to a fixed carrier either before or after its linkage to further oligonucleotides of the primary strand. This allows a separation of the hapten-coupled strand from all precursors and by-products without hapten, e.g. under denatured conditions (e.g. pH 13). The respectively selected hapten-carrier combination must be stable under the conditions set. A preferred hapten is e.g.

biotin which is bound by strepavidin coupled to a carrier. Furthermore, the oligonucleotides can be coupled with antigens which are recognized and bound by antibodies fixed to a carrier. The further synthesis of the primary strand or one of the further steps described in the following can then be carried out on said carrier. The second hapten could e.g. be useful for detection methods to be carried out with the nucleic acid polymer at a later time.

In a further preferred embodiment a polymerase enzyme is added to the reaction batch of a synthesis reaction carried out according to the present method to form a nucleic-acid double strand from the primary strand, which is a nucleic-acid single strand, or to amplify the complementary strand (i.e. the counter strand to the primary strand) in a purposeful manner (asymmetrical PCR). An oligonucleotide which is complementary to the 3' end of the complete primary strand (reverse primer) serves as the specific primer.

In a preferred embodiment the reaction batch of a synthesis reaction performed according to the present method has added thereto a polymerase enzyme and, in addition, terminal forward and reverse primers in excessive amounts with respect to the synthesis product used. Double-stranded nucleic acid, polymers are thereby formed from the single-stranded nucleic acid polymers under the principle of the polymerase chain reaction (Saiki et al., Science 239, 487–491, 1988).

The polymerase enzyme is here selected from the group of the DNA polymerases, e.g. *E. coli* polymerase I, Klenow polymerase, T4 DNA polymerase and reverse transcriptase. The nucleic-acid double strands formed thereby may either be DNA-DNA double strands or DNA-RNA double strands (Kleppe et al., Proc., Natl. Acad. Sci. 67, 68–79,1970).

In a particularly preferred embodiment the added polymerase is a temperature-stable polymerase, e.g. Taq polymerase. Even after several temperature cycles the temperature-stable enzyme will hardly lose any of its activity and can therefore catalyze the polymerase reaction of several successive cycles.

The polymerase reaction is preferably repeated several times to exponentially amplify the nucleic-acid double strand. In accordance with the principle regarding polymerase chain reaction each cycle comprises a denaturation of already existing nucleic-acid double strands by taking standard measures, e.g. by increasing the temperature or the pH, annealing the terminal primer under suitable conditions or a polymerase-catalyzed nucleic acid synthesis. In the case of a temperature-stable polymerase the addition of further polymerase is not necessary; however, in cases where one of the polymerases that are not temperature-stable has been used for the polymerization reaction, said polymerase is inactivated by thermal denaturation; in such a case fresh polymerase enzyme has to be added in each cycle. Normally, the polymerase reaction is carried out 5 to 15 times, preferably about 8 to 12 times. The essential advantage offered by repeating the polymerase reaction is that on account of the position of the primers (terminal), purposefully complete synthesis product can be amplified in an exponential manner.

The double strands are normally denatured at temperatures of more than 90° C. The reaction batch is then slowly cooled so that, depending on their composition, the terminal primers can hybridize—at temperatures ranging from 80° C. to 45° C.—with the single strands that will then be present. The polymerase-catalyzed DNA synthesis can be carried out using a temperature-stable enzyme, whereby the formation of unspecific hybrids is minimized.

Figure 4:
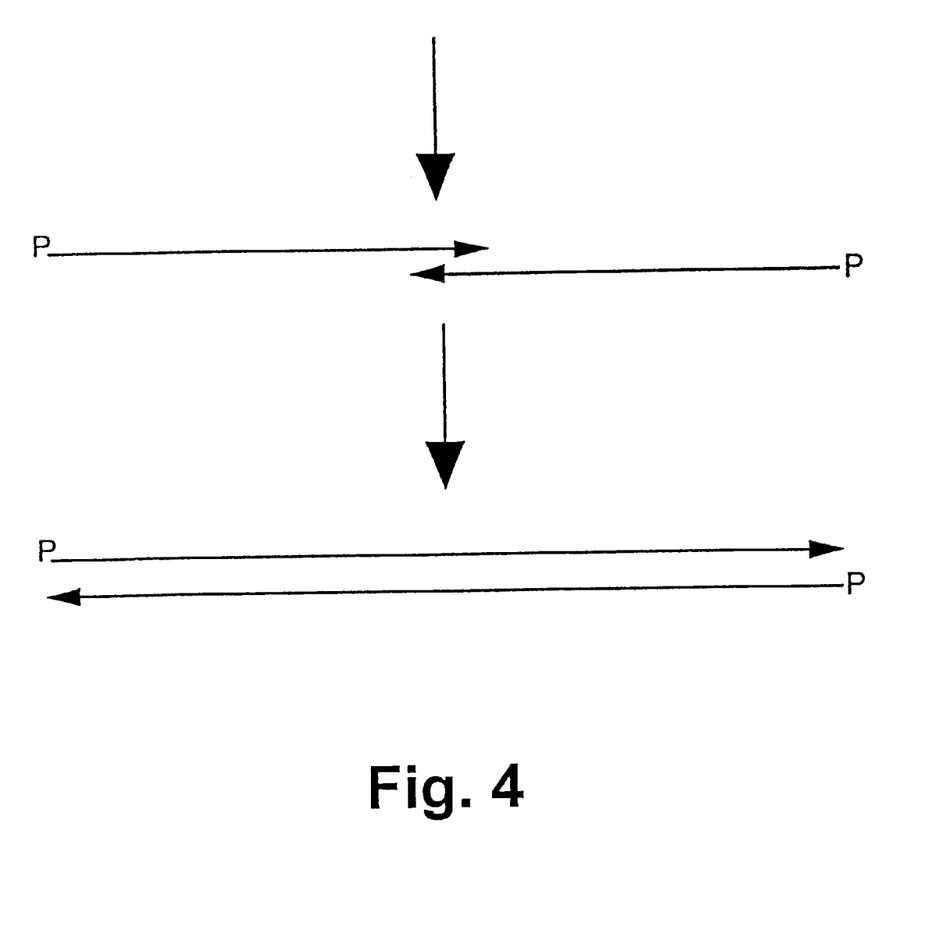
FIG. 4 shows the principle of the fill-in method by way of two long oligonucleotides that are only complementary in their 3' region. By way of hybridization of the complementary 3' regions, the 3' end of each of the oligonucleotides serves as a primer for a polymerase reaction along the template of the respectively other oligonucleotide.

The subject matter of the present invention is further a single-stranded nucleic acid polymer which has been obtained with the method according to the invention. By skillfully coupling the method of the invention (by which single-stranded primer strands are first produced) with the fill-in method, it is easily possible to produce double-stranded nucleic acid polymers of several 1000 bases (FIG. 4). To this end the primary strands, for instance, have to be conceived such that they are complementary to one another at their 3' ends within a range of a few base pairs, e.g. 20 to 60, preferably 30 to 40 base pairs, so that in a polymerase reaction subsequently taking place in vitro or in vivo the 3' end of each primary strand can serve as a primer for a template-dependent polymerase.

The following figures and the example will explain the invention.

First of all, phosphorylated oligonucleotides are provided for the primary strand and non-linkable oligonucleotides for the complementary strand, with the non-linkable oligonucleotides being complementary to the oligonucleotides of the primary strand and overlapping with two respective ones of the phosphorylated oligonucleotides (a). Subsequent ligation results in a single-stranded nucleic acid polymer (b), the primary strand.

EXAMPLE

Synthesis of an Algae-adapted Gene Coding for Green Fluorescent Protein (GFP) from the Jellyfish *Aguorea victorea*.

Figure 5A:
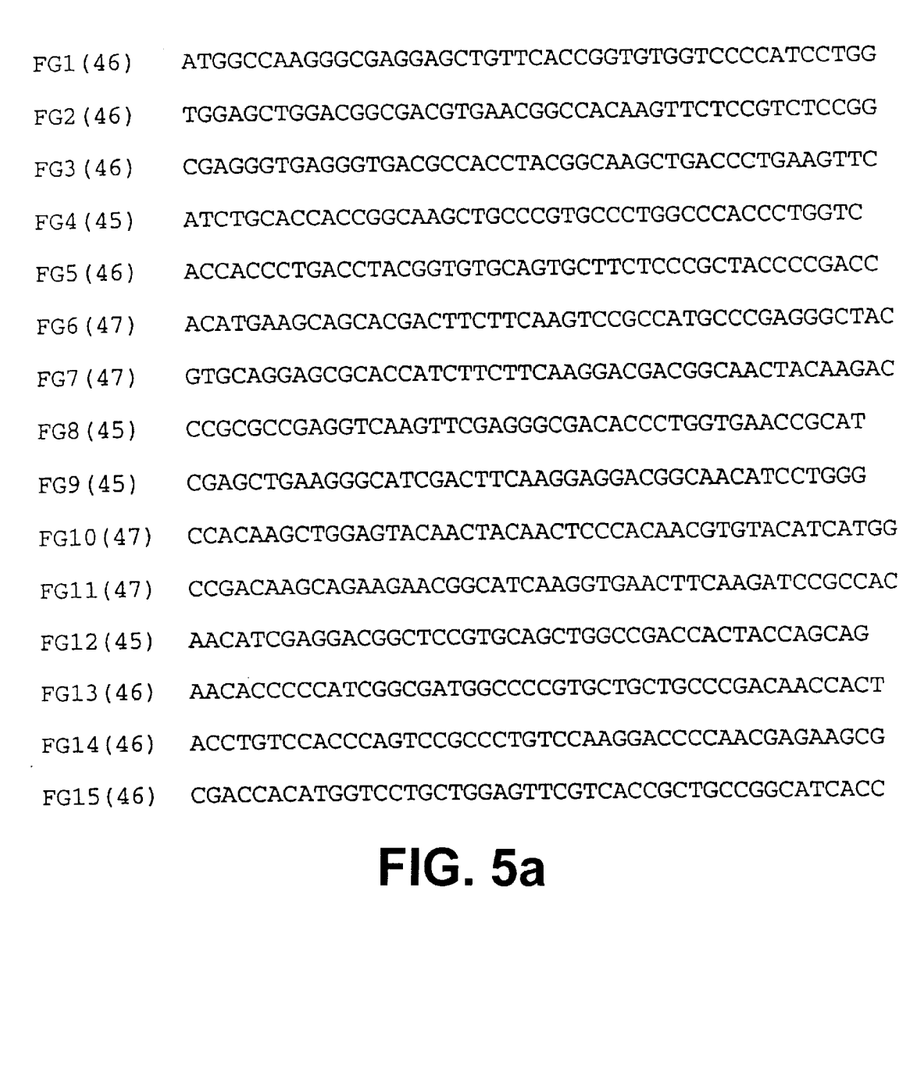
FIG. 5
a) oligonucleotides for the synthesis of the primary strand of the algae-adapted GFP mutant S65T/F64L (FG1 to FG15) corresponding to SEQ ID. NOS: 1–15, respectively;
b) oligonucleotides of the complementary strand (non-linkable) (FG14rev to FG1rev)(corresponding to SEQ ID NOS: 16–29,respectively;
c) oligonucleotide FG15rev (SEQ ID NO: 30), primer for the polymerase-catalyzed synthesis of the complementary strand.
Figure 5B:
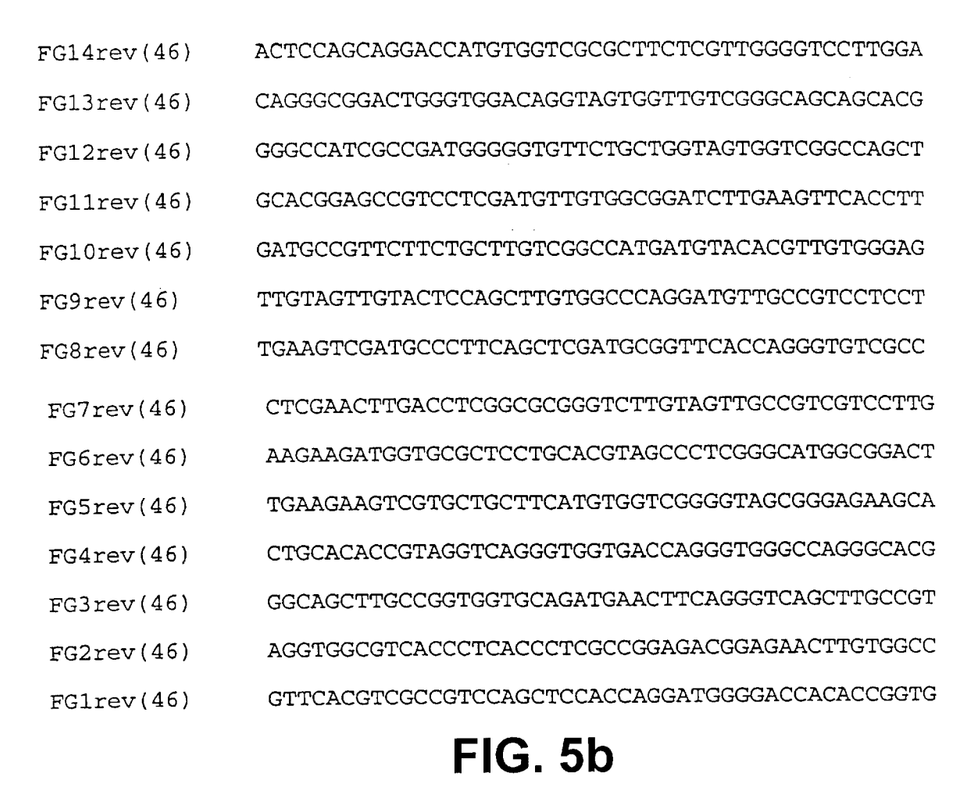

The synthesis of a modified gene (SEQ ID NO: 31) for green fluorescent protein (GFP) from the jellyfish *Aguorea victorea* shall be shown in the following. The codon use is modified in the synthetic gene such that the codons of green algae, such as Chlamydomonas, are preferred. 30 oligonucleotides with a length of 45 to 50 bases were used for synthesis. The oligonucleotides of the primary strand are designated as FG1 to FG15 (SEQ ID NO: 1–15) and have a length of 45 to 47 bases. The non-linkable oligonucleotides of the complementary strand are designated as FG14rev to FG1rev (SEQ ID NO:16–29) and have a length of 46 bases (FG14rev to FG1rev). The sequences of the oligonucleotides are shown in FIGS. 5a, b.

The reaction was carried out in a programmable thermocycler. The oligonucleotides which form the linkable strand were phosphorylated at the 5' end prior to synthesis reaction.

Step 1
Oligonucleotide Phosphorylation at the 5' end (100 μl Batch)
10 μl oligonucleotides FG1 to FG15 (500 pmole total, equal molar concentration of each oligonucleotide)
10 μl kinase buffer (10-fold concentration, Biolabs)
10 μl ATP 2 mM
69 μl H$_2$O
1 μl T4 polynucleotide kinase (10 units Biolabs)

The reaction was carried out at 37° for 4 h and subsequently completed by incubation at 95° C. for 5 minutes.

Step 2
Carrier-free Nucleotide Polymer Synthesis (Primary Strand)

The reaction was carried out in a programmable thermocycler. Recombinant Pfu DNA ligase of the company Stratagene was used. The buffer conditions were adapted to the ligase conditions with KCl, NP-40, MgCl$_2$, the ions being taken into account in the kinase batch.

10 μl 5'-phosphorylated oligonucleotides (50 pmole total) from step 1 (FG1-FG15)
1 μl non-phosphorylated oligonucleotides (50 pmole total) (FG1rev-FG14rev)
6 μl KCl (100 mM)
3 μl NP-40 (0.5%)
4 μl MgCl$_2$ (50 mM)
3 μl ATP (10 mM)

The reaction batch was incubated at 95° C. for 3 minutes and at 80° C. for 3 minutes. During incubation at 80° C., 32 μl Pfu DNA ligase (12 units of thermostable ligase of the company Stratagene) were added and the following temperature cycle was subsequently carried out 3 times:

a) 95° C. for 1 minute
b) cooling from 95° C. to 70° C. within 1 minute
c) linear cooling from 70° C. to 55° C. over a period of 1 hour
d) incubating at 55° C. for 2 hours.

Variant 1

The product is precipitated for separating the Pfu ligase, optionally amplified via PCR and Taq polymerase and cloned.

Variant 2

To facilitate the separation, the primer FG1 is used in biotinylated form.

After termination of the synthesis the reaction batch is set to pH 13 with NaOH. Streptavidin magnetic beads (Dynal) are added and the synthesis product is retained with a magnet on the wall of the reaction vessel while all reverse primers, non-consumed forward primers and ligase are removed with the supernatant. The clean synthesis product which is now coupled to streptavidin is received in 30 μl of a neutral buffer and can e.g. be amplified as in step 3 (see below).

Step 3
Amplification of the Synthesis Product with the Help of the Polymerase Chain Reaction (PCR)

Variant 1

Figure 5C:
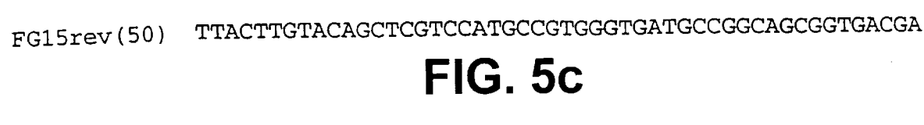
Figure 6:
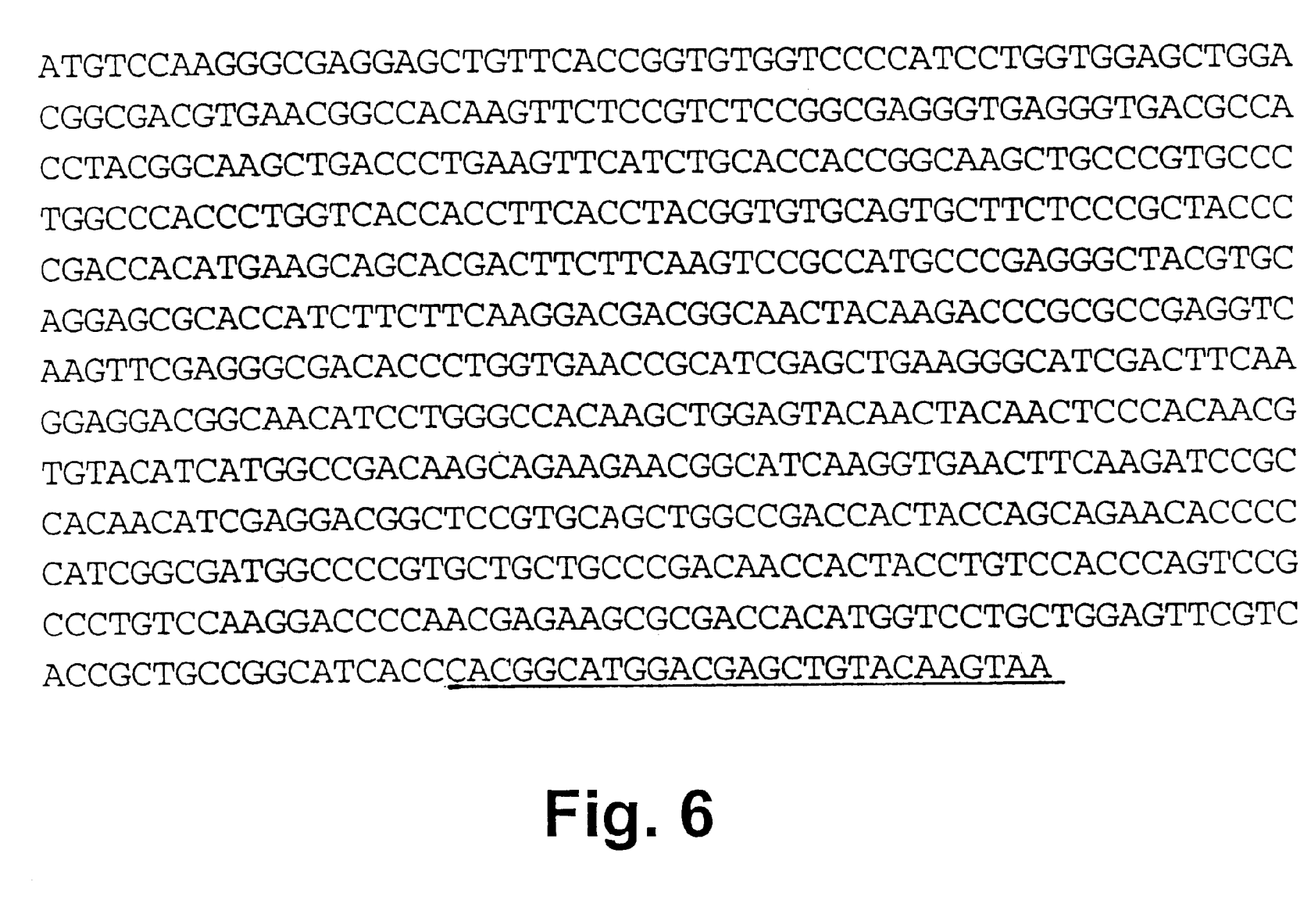
FIG. 6 modified gene (S65T/F64L)(SEQ ID NO: 31) for the green fluorescent protein (GFP) from *Aquorea victorea*. In comparison with the natural GFP gene, the gene was modified such that it only contains codons which are preferred by green algae, for instance Chiamydomonas. The underlined nucleotides were first filled by polymerase reaction (template: FG15rev).

1 μl of the synthesis product is amplified with 1 unit of thermostable Pfu polymerase (Stratagene) in 12 cycles in the standard buffer (according to the manufacturer) in a 50 μl batch. The olignucleotide FG1 serves as forward primer, the oligonucleotide FG15rev (50 bases; SEQ ID NO: 30 FIG. 5c) serves as reverse primer. Final concentration: 25 pmole per 50 μl.

Variant 2

For amplification by means of PCR two terminal primers are added that although they have a total length of 30 bases and 33 bases, respectively, only 21 bp and 24 bp, respectively, of said primers hybridize with the synthesis product. Each of the "overhangs" contains a cleavage site of the "multiple cloning region" of the vector pBenescript II KS (Stratagene). The amplified product is cut with the enzymes XhoI and KnpI, purified via Quiaex II (Quiagen) and cloned in the standard manner.

Forward primer with XhoI site: (SEQ ID NO: 32):

5' CCG <u>CTC GAG</u> ATG GCC MG GGC GAG GAG CTG reverse primer with KpnI site: (SEQ ID NO: 33):

5' CGC <u>GGA TCC</u> TTA CTT GTA CAG CTC GTC CAT GCC

What is claimed is:

1. Method for producing a nucleic acid polymer, comprising the steps of:
   a) providing 2 or more linkable oligonucleotides which in a continuous arrangement and after linkage are able to form a primary strand, and 2 or more non-linkable oligonucleotides, each of the non-linkable oligonucleotides comprising two adjoining regions the first of which is complementary only to the 3' end of a first linkable oligonucleotide and the second of which is complementary only to the 5' end of a second linkable oligonucleotide;
   b) hybridizing oligonucleotides for the primary strand with the complementary regions of the non-linkable oligonucleotides; and
   c) linking the oligonucleotides of the primary strand, thereby producing a nucleic acid polymer.

2. Method for producing a nucleic acid polymer, comprising the steps of:
   a) providing linkable oligonucleotides which in a continuous arrangement and after linkage are able to form a primary strand, and non-linkable oligonucleotides, each of the non-linkable oligonucleotides comprising two adjoining regions the first of which is complementary only to the 3' end of a first linkable oligonucleotide and the second of which is complementary only to the 5' end of a second linkable oligonucleotide;
   b) hybridizing oligonucleotides for the primary strand with the complementary regions of the non-linkable oligonucleotides; and
   c) linking the oligonucleotides of the primary strand, thereby producing a nucleic acid polymer,
   wherein the number of linkable oligonucleotides is 4 or more, and the number of non-linkable oligonucleotides is equal to, one higher, or one lower, than the number of linkable oligonucleotides.

3. Method according to claim 1, comprising one or several repetitions of steps (b) and (c), wherein denaturation is carried out prior to each repetition.

4. Method according to claim 3, wherein steps (b) and (c) are repeated 1 to 8 times.

5. Method according to claim 1, wherein the oligonucleotides of the primary strand are enzymatically linked.

6. Method according to claim 5, wherein thermostable ligase is added for enzymatic linkage.

7. Method according to claim 5, wherein hybridizing and linking are carried out between 45° C. and 80° C.

8. Method according to one of claims 1, 3, and 4, wherein the oligonucleotides of the primary strand are linked chemically.

9. Method according to one of claims 1, 3, and 4, wherein the oligonucleotides of the primary strand are linked photochemically.

10. Method according to one of claims 1 and 3–7, wherein the non-linkable oligonucleotides are not phosphorylated.

11. Method according to one of claims 1 and 3–7, wherein the 3' end or the 5' end of the non-linkable oligonucleotides is modified.

12. Method according to claim 1, wherein each of the linkable and non-linkable oligonucleotides comprises 30 to 1500 nucleotides.

13. Method according to claim 1, wherein each of the linkable oligonucleotides comprises 30 to 200 nucleotides.

14. Method according to claim 13, wherein the non-linkable oligonucleotides comprise 30 to 50 nucleotides.

15. Method according to claim 1, wherein the regions of complementarity between linkable oligonucleotides of the primary strand and non-linkable oligonucleotides have each a length of about 15 to 30 bp.

16. Method according to claim 1, wherein prior to steps (a) to (c) according to claim 1 the terminal oligonucleotides for the primary strand and/or oligonucleotides which are fully or partly complementary to the terminal oligonucleotides for the primary strand are annealed to the ends of a linearized vector and linked to said ends.

17. Method according to claim 1, wherein the 3' terminal oligonucleotide for the primary strand carries a hapten at the 3' end and/or the 5' terminal oligonucleotide for the primary strand carries a hapten at the 5' end.

18. Method according to claim 1, further comprising the steps of:
   d) adding a polymerase to form a nucleic-acid double-strand polymer, and
   e) carrying out a polymerase reaction.

19. Method according to claim 15, wherein prior to or after addition of polymerase in step d), an oligonucleotide complementary to the 3' end of the complete primary strand (reverse primer) or terminal forward and reverse primers are additionally added.

20. Method according to any one of claims 15 to 18, wherein the added polymerase is a temperature-stable polymerase.

21. Method according to claim 18, comprising one or more repetitions of step (e), wherein denaturation is carried out prior to each repetition.

22. Method according to claim 21, wherein denaturation is carried out at temperatures of more than 90° C., and annealing of terminal primers and the polymerase-catalyzed DNA synthesis are carried out at 45° C. to 70° C.

23. Method according to claim 7, wherein hybridizing and linking are carried out at 70° C.

24. Method according to claim 15, wherein the regions of complementarity between linkable oligonucleotides of the primary strand and non-linkable oligonucleotides each have a length of about 20 to 25 bp.

25. Method according to claim 4, wherein steps (b) and (c) are repeated 3 to 5 times.

26. Method according to claim 13, wherein each of the linkable oligonucleotides comprises 30 to 60 nucleotides.

27. Method according to claim 3, wherein the oligonucleotides of the primary strand are enzymatically linked.

28. Method according to claim 4, wherein the oligonucleotides of the primary strand are enzymatically linked.

29. Method according to claim 6, wherein hybridizing and linking are carried out between 45° C. and 80° C.

30. Method according to claim 1, wherein 4 or more linkable oligonucleotides, and three or more non-linkable oligonucleotides, are provided.

31. Method according to claim 2, wherein each non-linkable oligonucleotide corresponds to a segment of a strand complementary to the primary strand.

32. Method according to claim 31, wherein the combined length of the non-linkable oligonucleotides placed end-to-end is less than the length of the primary strand.

* * * * *